United States Patent [19]

Edge et al.

[11] 4,304,788
[45] Dec. 8, 1981

[54] HYDROXYALKANOIC ACID DERIVATIVES

[75] Inventors: Michael D. Edge, Congleton; Wilson S. Waring, Macclesfield, both of England

[73] Assignee: Imperial Chemical Industries Limited, London, England

[21] Appl. No.: 220,718

[22] Filed: Dec. 29, 1980

Related U.S. Application Data

[63] Continuation of Ser. No. 66,468, Aug. 13, 1979, abandoned.

[30] Foreign Application Priority Data

Sep. 8, 1978 [GB] United Kingdom ............ 36173/78

[51] Int. Cl.$^3$ .................. A61K 31/59; A61K 31/235; C07C 69/76; C07C 51/16
[52] U.S. Cl. .................................. 424/308; 424/317; 560/102; 562/409; 562/418
[58] Field of Search ................ 424/308, 317; 560/102; 562/409, 418

[56] References Cited

FOREIGN PATENT DOCUMENTS 140246   8/1965  United Kingdom .
1098111  1/1968  United Kingdom .
112107   7/1968  United Kingdom .
1140748  1/1969  United Kingdom .
1435050  5/1976  United Kingdom .
1499508  2/1978  United Kingdom .

Primary Examiner—Stanley J. Friedman
Attorney, Agent, or Firm—Cushman, Darby & Cushman

[57] ABSTRACT

The invention concerns novel hydroxyalkanoic acid derivatives of the formula:

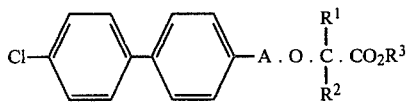

in which A is a straight or branched chain (2–6C)alkylene, $R^1$ and $R^2$ are independently hydrogen or (1–6C) alkyl, and $R^3$ is hydrogen or (1–6C)alkyl, and when $R^3$ is hydrogen, base-addition salts thereof; and processes for their manufacture.

The compounds possess useful anti-arthritic properties and the invention also concerns pharmaceutical compositions of such compounds for use in the treatment of arthritic joint diseases. A representative compound of the invention is 2-{2-[4-(4-chlorophenyl)phenyl]-ethoxy}propionic acid.

7 Claims, No Drawings

HYDROXYALKANOIC ACID DERIVATIVES

This is a continuation, of application Ser. No. 66,468 filed Aug. 13, 1979, now abandoned.

This invention relates to novel hydroxyalkanoic acid derivatives and, more particularly, it relates to hydroxyalkanoic acid derivatives which possess useful anti-arthritic properties, to pharmaceutical compositions thereof for use in the treatment of arthritic joint diseases, and to processes for the manufacture of said derivatives.

It is known from our earlier work that various phenylalkoxyacetic acids possess the property of lowering the level of at least one factor believed to be involved in atherosclerotic disease, for example the level of serum cholesterol, serum triglycerides or plasma fibrinogen, and also possess anti-inflammatory properties (U.K. patent specification Ser. No. 1121027). We have now discovered, and herein lies our invention, that the introduction of a 4-chlorophenyl substituent into the para-position of the phenyl radical of these compounds gives rise to new compounds having unexpected anti-arthritic properties.

According to the invention there is provided a hydroxyalkanoic acid derivative of the formula:

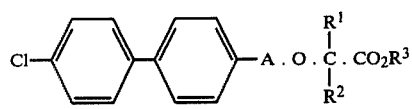

wherein A is a straight or branched chain (2-6C)alkylene diradical, $R^1$ and $R^2$ are independently hydrogen or (1-6C)alkyl radicals, and $R^3$ is hydrogen or a (1-6C)alkyl radical; or, when $R^3$ is hydrogen, a pharmaceutically acceptable base-addition salt thereof.

It will be observed that those compounds of formula I wherein $R^1$ and $R^2$ are different or wherein A is an asymmetrically branched alkylene diradical, possess at least one asymmetric carbon atom and as such can be isolated in a racemic form and in two optically active forms. This specification is addressed to the racemic form of compounds of formula I containing an asymmetric carbon atom and to any optically active form which possesses the above useful properties; it being a matter of common general knowledge in the art how to resolve a racemic form, or how to synthesise an optical isomer from an optically active starting material, and how to determine the biological properties of the optical isomers.

A particular value for $R^1$ or $R^2$ when it is a (1-6C)alkyl radical is, for example, a methyl, ethyl, propyl, isopropyl or butyl radical.

A particular value for $R^3$ is, for example, hydrogen, or a methyl or ethyl radical.

A particular value for A when it is a straight chain (2-6C)alkylene diradical is, for example, an ethylene or trimethylene diradical; and when it is a branched chain (2-6C)alkylene diradical is, for example, an ethylidene, propylidene, 2-methylpropylidene or butylidene diradical.

A particular base-addition salt of a compound of formula I wherein $R^3$ is hydrogen is, for example, an alkali metal or alkaline earth metal salt, for example a sodium, potassium, calcium or magnesium salt, an aluminium salt, for example an aluminium hydroxide disalt, an ammonium salt, or a salt of an organic base affording a pharmaceutically acceptable cation, for example triethanolamine or tris(hydroxymethyl)methylamine.

A preferred value for $R^3$ is hydrogen.

A particular group of compounds of the invention comprises those compounds of formula I wherein A is a branched chain (2-6C)alkylene diradical, $R^2$ is hydrogen, and $R^3$ is hydrogen or a (1-4C)alkyl radical, for example a methyl or ethyl radical; and, when $R^3$ is hydrogen, the pharmaceutically acceptable base-addition salts thereof.

A further particular group of compounds of the invention comprises those compounds of formula I wherein A is a straight chain (2-6C)alkylene diradical, especially an ethylene diradical, $R^2$ is hydrogen, and $R^3$ is hydrogen or a (1-4C)alkyl radical, for example a methyl or ethyl radical; and, when $R^3$ is hydrogen, the pharmaceutically acceptable base-addition salts thereof.

Specific compounds of the invention are described hereinafter. Of these, a preferred compound is 2-{2-[4-(4-chlorophenyl)phenyl]ethoxy}propionic acid, or a pharmaceutically acceptable base-addition salt thereof.

The compounds of formula I may be manufactured by an chemical process which is known to be applicable to the synthesis of chemically analogous compounds. Such processes are provided as a further feature of the invention and are exemplified by the following in which $R^1$, $R^2$, $R^3$ and A have the meanings defined above unless stated otherwise:

(a) Reacting a base-addition salt of a compound of the formula

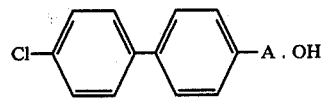

with a halogenated compound of the formula:

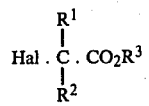

wherein Hal. is a chloro, or iodo radical.

A particularly suitable base-addition salt of a compound of formula II is, for example, an alkali metal salt, for example a sodium or potassium salt. The required salt of a compound of formula II is preferably preformed by reaction of a compound of formula II with a suitable base, for example an alkali metal hydride or (1-6C)alkoxide, for example sodium hydride or ethoxide, conveniently in a suitable solvent which may also function as solvent for the reaction with the halogenated compound of formula III. A particularly suitable solvent when an alkali metal hydride is used as the base, is, for example, dimethylformamide, and when an alkali metal (1-6C)alkoxide is used, is, for example, the corresponding (1-6C)alkanol.

Alternatively, the base addition salt of a compound of formula II may be formed during the reaction by using a compound of formula II as starting material instead of its salt, and carrying out the reaction with the halogenated compound of formula II in the presence of a suitable base and suitable solvent as defined above.

The process may be carried out, for example, at 0° to 100° C., and particularly conveniently, at 15° to 30° C., and is conveniently performed in a suitable inert solvent, for example dimethylformamide, dimethylsulphoxide, or hexamethylphosphoramide, optionally together with, for example, tetrahydrofuran. Alternatively, a (1–6C)alkanol, for example ethanol, may be used as solvent, it being understood that when $R^3$ is a (1–6C)alkyl radical which does not correspond to the (1–6C)alkanol which is used as solvent, then some ester exchange may occur.

It will be recognised that when $R^3$ is hydrogen it is necessary to employ at least two molecular equivalents of the base-addition salt of the compound of formula II.

(b) Reacting a compound of the formula:

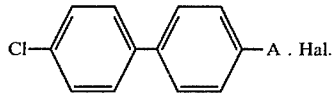

IV wherein Hal. is a chloro, bromo or iodo radical, with a base-addition salt of a compound of the formula:

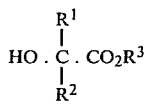

V

This process is particularly suitable for the compounds of formula I wherein A is a straight chain (3–6C-)alkylene diradical.

A particularly suitable base-addition salt of a compound of formula V is, for example, an alkali metal salt, for example a sodium or potassium salt, or, when $R^3$ is hydrogen is, for example, a di-alkali metal salt, for example a di-sodium or di-potassium salt.

The required salt of a compound of formula V may either be pre-formed by reaction with a suitable base in a suitable solvent as defined hereinabove for process (a), or it may be formed during the reaction using similar conditions to those also described hereinabove.

(c) For a compound of formula I wherein $R^3$ is hydrogen, hydrolysing a compound of the formula:

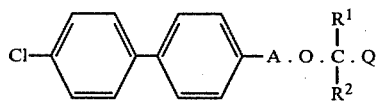

VI wherein Q is a (1–6C)alkoxycarbonyl, benzyloxycarbonyl, phenoxycarbonyl or cyano radical.

A particularly suitable value for Q when it is a (1–6C-)alkoxycarbonyl radical, is for example, a methoxycarbonyl or ethoxycarbonyl radical.

The hydrolysis is conveniently carried out, for example, by reacting the compound of formula VI with a suitable base, for example sodium hydroxide or potassium hydroxide in an organic solvent, for example methanol or ethanol, optionally mixed with water. The hydrolysis may be carried out, for example, at 15° to 100° C., and is particularly conveniently carried out at 60° to 80° C.

The necessary starting materials of formula VI wherein Q is other than a cyano radical may be conveniently obtained using the procedure and general reaction conditions of process (a) but employing the sodium salt of a compound of formula II and a bromo derivative of the formula:

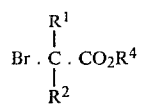

VII wherein $R^4$ is a (1–6C)alkyl, benzyl or phenyl radical, as reactants.

The corresponding cyano compounds of formula VI may be obtained in a similar manner but replacing the compound of formula VII by a bromo compound of the formula:

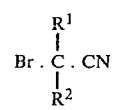

VIII (d) For a compound of formula I wherein $R^3$ is a (1–6C)alkyl radical, esterifying a compound of formula I wherein $R^3$ is hydrogen (hereinafter referred to as an acid of formula I).

The esterification may be carried out by any general procedure known for the preparation of analogous compounds.

Thus, an acid of formula I, or a reactive derivative thereof, may be reacted with a (1–6C)alkanol, for example methanol or ethanol.

When a reactive derivative is used, the process is preferably carried out in the presence of a suitable base, for example pyridine or triethylamine, and, conveniently, in an inert solvent, for example chloroform, methylene chloride, diethyl ether or tetrahydrofuran, and at a temperature of, for example, 0° to 100° C., and preferably, at 15° to 30° C. A particularly suitable reactive derivative of an acid of formula I is, for example, an acid halide such as an acid chloride or bromide, an acid azide, an acid anhydride, or a mixed anhydride derived from an acid of formula I and a (1–4C)alkanoic acid, such as acetic anhydride.

When an acid of formula I is used as starting material the esterification may be carried out:

(i) in the presence of a condensing agent such as dicyclohexylcarbodiimide, preferably under essentially anhydrous conditions and at a temperature of, for example 15° to 30° C., for an extended period and in an inert solvent as defined above; or (ii) in the presence of a strong acid catalyst such as sulphuric, hydrochloric or toluene p-sulphonic acid, and in which case the (1–6C)alkanol may conveniently be used in excess and the process may conveniently be carried out at the boiling point of the reaction mixture, for example, at 40° to 100° C.

Whereafter, when a pharmaceutically acceptable base-addition salt of an acid of formula I is required said acid is reacted using conventional procedures with the required base affording a pharmaceutically acceptable cation. Thus, for example, an acid of formula I may be neutralised by reaction with a stoichiometric amount of the appropriate base in water and then evaporated to yield the required base-addition salt. Alternatively, an aqueous solution of a water soluble base-addition salt of an acid of formula I, such as an ammonium salt, may be reacted with an aqueous solution of a salt of another base forming a water insoluble base-addition salt with the acid of formula I, for example with calcium chloride. The insoluble salt may then be collected by filtration.

When an optical isomer is required, the racemic form of an acid of formula I is resolved by reaction with an optically active base, for example (+) or (−)-α-methylbenzylamine, and then if required, subsequently esterified by process (d) hereinabove, or one of processes (a)–(c) is carried out using an optically active starting material.

The starting materials required for the above processes may be obtained by standard procedures of organic chemistry and as described in the accompanying Examples.

As stated above the compounds of formula I possess useful anti-arthritic properties, which may be demonstrated by the following standard laboratory procedure based on that devised by Newbould (*Brit.J.Pharmacol.* 1963, 21, 127–136). The procedure involves inducing arthritis in rats by intradermal injection of a suspension of heat-killed tubercle bacilli in paraffin oil into one hind foot pad of each rat, and then measuring the effects of daily oral dosing of a test compound on the increase in thickness of the injected foot, and on the inhibition of the rise of $\alpha_1$-acid glycoproteins in the blood serum, in both cases after at least 21 days. Using this test procedure the compounds of formula I produce significant activity at a daily dose of 100 mg./kg. or much less, and without any overt toxic effects. Thus, for example, the novel compound 2{2-[4-(4-chlorophenyl)phenyl]ethoxy}propionic acid produced a significant reduction in the increase in foot thickness of the injected foot after 21 days oral dosing at 5 mg./kg., without any overt toxic or other untoward effects being observed.

Whilst not wishing to be bound by any particular theory as to the mode of action of the compounds of formula I, it is considered that their activity is due to a fundamental effect on the arthritic disease processes producing the tissue damage rather than to a mere palliative effect on the resultant inflammation produced by the arthritis.

It is therefore envisaged that the compounds of the invention will be of value in the treatment of other diseases of connective tissues, such as atherosclerosis, in addition to their use in the treatment of arthritic joint diseases such as rheumatoid arthritis, psoriatic arthritis, and ankylosing spondilitis.

When used to produce anti-arthritic effects in warm-blooded animals, the compounds of formula I will generally be administered at a daily oral dose in the range, for example 1 to 50 mg./kg. By way of example, in man this is likely to result in a total daily dose of from 50 to 2500 mg., given if necessary in divided doses.

The compounds of the invention may be administered in the form of pharmaceutical compositions and according to a further feature of the invention there is provided a pharmaceutical composition which comprises a compound of formula I in pharmaceutically acceptable form.

By "pharmaceutically acceptable form" is meant either a pharmaceutical preparation in which the compound is associated with a pharmaceutically acceptable diluent, or a pharmaceutical preparation, for example a capsule, in which the compound is confined in a unit dosage form without necessarily being associated with a diluent.

Preferred pharmaceutically acceptable forms are those suitable for oral administration, for example tablets, capsules, suspensions, solutions, syrups or elixirs. However, forms suitable for parenteral administration, for example sterile aqueous injections or suppositories, may also be employed. The compositions may be obtained by conventional procedures and, if desired, using conventional diluents or excipients. Dosage forms should preferably contain from 50 to 500 mg. of compound of a formula I per dosage unit.

When used in the treatment of inflammatory joint diseases the compositions of the invention may also contain one or more additional agents which can have a beneficial effect on the disease or on associated conditions, for example an agent selected from the following:
   an anti-inflammatory or analgesic agent, for example, acetyl-salicyclic acid, paracetamol, dextropropoxyphene, codeine, phenylbutazone, indomethacin, ibuprofen, ketoprofen, naproxen or sulindac;
   an anti-inflammatory steroid, for example prednisolone;
   an organo-gold derivative;
   a uricosuric agent, for example probenecid; chloroquine; and D-pencillamine.

The invention is illustrated by the following non-limiting Examples in which:
(i) all evaporations, unless otherwise stated, were carried out by rotary evaporation in vacuo;
(ii) reactions stated as carried out at room temperature were performed at a temperature of 18°–25° C.;
(iii) petroleum ether of b.p. 40°–60° C. is referred to as "petrol (40–60)" and other petroleum ether fractions are referred to correspondingly; and
(iv) yields (where given) are purely illustrative and are not to be construed as the maximum attainable for the process illustrated.

EXAMPLE 1

Potassium hydroxide (5.5 g.) was added to a solution of ethyl 2-{2-[4-(4-chlorophenyl)phenyl]-ethoxy}propionate (7.0 g.) in methanol (50 ml.), and the resultant solution was heated under reflux for 2 hours. The mixture was cooled and solvent removed by evaporation, the residue was mixed with water (50 ml.) and the solution obtained was extracted with ether (2×50 ml.) to remove non-acidic material. The aqueous phase was acidified with 4 N-hydrochloric acid to pH 2–3 and extracted with ethyl acetate (3×50 ml.). The extracts were washed with water, dried (MgSO$_4$) and evaporated. The oil obtained, solidified on trituration with hexane to give 2-{2-[4-(4-chlorophenyl)phenyl]-ethoxy}propionic acid (3.9 g., 57%), m.p. 90°–92° C. (after recrystallisation from a mixture of hexane and toluene), molecular ion: M+ 304.

The above mentioned substituted propionate was obtained as follows:

Sodium hydride (0.8 g., 80% w/w dispersion in mineral oil) was added to a stirred solution of 2-[4-(4-chlorophenyl)phenyl]-ethanol (5.0 g.) in dimethylformamide (20 ml.). The mixture was stirred at room temperature under nitrogen for 5 hours. Ethyl 2-bromopropionate (3 ml.) was then added and the mixture was stirred at room temperature. After 18 hours the mixture was partitioned between ethyl acetate (100 ml.) and 4-N-hydrochloric acid (100 ml.). The organic phase was separated, washed with water (30 ml.), and evaporated to give ethyl 2-{2-[4-(4-chlorophenyl)phenyl]ethoxy}-propionate as an oil (7.0 g.).

The substituted ethanol was obtained as follows:

Borane-methylsulphide complex (12 ml.) was added to a stirred solution of 2-[4-(4-chlorophenyl)-phenyl]acetic acid (24.7 g.) in tetrahydrofuran (100 ml.), maintained at 4° C. and under an atmosphere of nitrogen. After 1 hour at 4° C., the reaction mixture was allowed to warm up to room temperature and was then stirred for an additional 20 hours. The excess borane was then decomposed by careful addition of water (50 ml.) to the stirred reaction mixture. Ethyl acetate (200 ml.) and a saturated aqueous solution of sodium hydrogen carbonate (200 ml.) was then added to the mixture. After separation, the organic phase was washed with water, dried (MgSO$_4$) and evaporated. The residue was recrystallised from a mixture of hexane and toluene to give 2-[4-(4-chlorophenyl)phenyl]-ethanol (21.5 g.), m.p. 113°–115° C.

EXAMPLES 2–4

In a similar manner to that described in Example 1, the following acids of formula I were obtained with isolation of their corresponding esters. Thus:

(Example 2): 2{2-[4-(4-chlorophenyl)phenyl]ethoxy}-butyric acid was obtained in 35% overall yield as a solid, m.p. 90°–92° C. (molecular ion: M+ 318), using an equivalent amount of ethyl 2-bromobutyrate instead of ethyl 2-bromopropionate, and with the intermediate isolation of the ester, ethyl 2-{2-[4-(4-chlorophenyl)-phenyl]ethoxy}butyrate;

(Example 3): 2-{2-[4-(4-chlorophenyl)phenyl]ethoxy}-valeric acid was obtained in 25% overall yield as a solid, m.p. 89°–90° C., (molecular ion: M+ 332), using an equivalent amount of ethyl 2-bromo-valerate instead of ethyl 2-bromopropionate, and with the intermediate isolation of the ester, ethyl 2-{2-[4-(4-chlorophenyl)phenyl]ethoxy}valerate;

(Example 4): 2-{2-[4-(4-chlorophenyl)phenyl]ethoxy}3-methyl-butyric acid was obtained in 7% overall yield as a solid, m.p. 91°–92° C. (molecular ion: M+ 332), using an equivalent amount of ethyl 2-bromo-3-methylbutyrate instead of ethyl 2-bromopropionate, and after chromatographic purification of the intermediate ester, ethyl 2-{2-[4-(4-chlorophenyl)phenyl]ethoxy}3-methylbutyrate on a column of silica gel using chloroform as eluant.

EXAMPLE 5

A solution of ethyl 2-{1-[4-(4-chlorophenyl)-phenyl]ethoxy}propionate (3.0 g.) in a mixture of ethanol (150 ml.) and water (5 ml.), containing sodium hydroxide (5.0 g.), was heated under reflux for 5 hours. The mixture was then evaporated and the residue diluted with water (50 ml.) and extracted with ether. The ether extract was discarded and the aqueous alkaline phase was acidified to pH 1–3 by addition of concentrated hydrochloric acid. The mixture was extracted thoroughly with ether. The combined extracts were washed with water, dried (MgSO$_4$), and evaporated. The residue was triturated with petrol (40–60) and the solid which formed was separated and recrystallised from toluene to give 2-{1-[4-(4-chlorophenyl)phenyl]ethoxy}propionic acid, m.p. 144°–146° C. in 26% yield.

The above mentioned substituted propionate was obtained as follows:

Sodium hydride (0.7 g., 80% w/w suspension in mineral oil) was added gradually to a stirred solution of 1-[4-(4-chlorophenyl)phenyl]ethanol (4.7 g.) in dry dimethylformamide (20 ml.), keeping the temperature below 40° C. After 30 minutes stirring ethyl 2-bromopropionate (2.6 ml.) was then added, keeping the temperature below 30° C. After stirring for 16 hours at room temperature, the mixture was poured into water (150 ml.), and the subsequent mixture was extracted with ether. The combined extracts were washed with water, dried (MgSO$_4$) and evaporated to give ethyl 2-{1-[4-(4-chlorophenyl)phenyl]ethoxy}propionate, as an oil (3.0 g.).

EXAMPLE 6

The procedure described in Example 5 was repeated using an equivalent amount of ethyl bromoacetate in place of ethyl 2-bromopropionate. There was thus obtained 2-{1-[4-(4-chlorophenyl)phenyl]ethoxy}acetic acid, m.p. 147°–149° C. (after recrystallisation from toluene), in 35% overall yield, and with intermediate isolation of the ester, ethyl 2-{1-[4-(4-chlorophenyl)-phenyl]ethoxy}acetate.

EXAMPLE 7

The procedure described in Example 5 was repeated using an equivalent amount of ethyl 2-bromobutyrate in place of ethyl 2-bromopropionate. There was thus obtained 2-{1-[4-(4-chlorophenyl)phenyl]ethoxy}butyric acid, m.p. 128°–130° C. [after recrystallisation from toluene/petol (100–120)] in 11% overall yield, and with intermediate isolation of the ester, ethyl 2-{1-[4-(4-chlorophenyl)phenyl]ethoxy}butyrate.

EXAMPLE 8

Sodium hydride (1 g., 50% w/w suspension in mineral oil) was added gradually to a stirred solution of 1-[4-(4-chlorophenyl)phenyl]propanol (4.9 g.) in dry dimethylformamide (20 ml.), keeping the temperature below 40° C. After 2 hours stirring ethyl bromoacetate (2.3 ml.) was then added, keeping the temperature below 30° C. After stirring for 16 hours at room temperature, the mixture was poured into water (150 ml.), and the subsequent mixture was extracted with ether. The combined extracts were washed with water, dried (MgSO$_4$) and evaporated to give ethyl 2-{1-[4-(4-chlorophenyl)-phenyl]propoxy}acetate as an oil (5 g.).

This oil was dissolved in a mixture of ethanol (100 ml.) and water (10 ml.) containing potassium hydroxide (5 g.), and heated under reflux for 2 hours. The mixture was evaporated and the residue diluted with water and acidified to pH 1–3 by addition of concentrated hydrochloric acid. The mixture was extracted with ether, and the combined extracts were shaken with dilute ammonium hydroxide. The alkaline extract was acidified with concentrated hydrochloric acid and extracted with ether. The combined extracts were dried (MgSO$_4$) and evaporated to give a solid residue (3.5 g.) which was recrystallised from toluene. There was thus obtained 2-{1-[4-(4-chlorophenyl)phenyl]propoxy}acetic acid, m.p. 170°–172° C. in 28% overall yield.

1-[4-(4-Chlorophenyl)phenyl]propanol used as starting material in the above procedure was obtained as follows:

A mixture of 4-(4-chlorophenyl)propiophenone (20 g.), ethanol (100 ml.) and sodium borohydride (5 g.) was stirred at room temperature for 3 hours, then poured into water (300 ml.) and filtered to give 1-[4-(4-chlorophenyl)phenyl]propanol as a solid residue (20 g.) m.p. 114°–116° C. This residue was dried in vacuo at 60° C. and was used without further purification. A sample recrystallised from ethanol had m.p. 117°–118° C.

4-(4-Chlorophenyl)propiophenone was obtained as follows:

Anhydrous aluminium chloride (36 g.) was added gradually to a stirred and cooled solution of 4-chlorobiphenyl (47 g.) in chlorobenzene (200 ml.) keeping the temperature at 0°-5° C. Stirring was continued for 30 minutes below 5° C. after the addition was complete. Propionyl chloride (23 ml.) was then added slowly to the stirred mixture keeping the temperature below 10° C. The mixture was stirred for 16 hours at room temperature, and then poured on ice (400 g.) and concentrated hydrochloric acid (130 ml.). The aqueous mixture was then heated to 60° C. The organic phase was separated and the aqueous phase was extracted with chlorobenzene (200 ml.). The combined organic phases were washed successively with water (200 ml.), sodium acetate solution (200 ml. of 10% w/v) and water (2×200 ml.). The chlorobenzene was removed by steam distillation, and the solid residue was separated and recrystallised from ethanol, giving 4-(4-chlorophenyl)-n-propiophenone, m.p. 109°-111° C.

EXAMPLE 9

The procedure described in Example 8 was repeated using an equivalent amount of ethyl 2-bromopropionate in place of ethyl bromoacetate. There was thus obtained 2-{1-[4-(4-chlorophenyl)phenyl]propoxy}propionic acid, m.p. 139°-143° C. [after recrystallisation from toluene/petrol (60-80)] in 19% overall yield.

EXAMPLE 10

The procedure described in Example 8 was repeated using an equivalent amount of 1-[4-(4-chlorophenyl)phenyl]-2-methylpropan-1-ol in place of 1-[4-(4-chlorophenyl)phenyl]propanol. There was thus obtained 2-{1-4-(4-chlorophenyl)phenyl]2-methylpropoxy}acetic acid, m.p. 163°-164° C. [after recrystallisation from ethyl acetate/petol (60-80)] in 20% overall yield.

The 1-[4-(4-chlorophenyl)phenyl]-2-methylpropan-1-ol used as starting material was obtained as follows:

A mixture of 4-(4-chlorophenyl)isobutyrophenone (18 g.), ethanol (200 ml.) and sodium borohydride (5 g.) was stirred at room temperature for 2 hours, then poured into water (1 l.) and filtered to give 1-[4-(4-chlorophenyl)phenyl]-2-methylpropan-1-ol as a solid residue (17 g.). This residue was dried in vacuo at 60° C. and was used without further purification. A sample recrystallised from aqueous ethanol had m.p. 71°-72° C.

4-(4-Chlorophenyl)isobutyrophenone was obtained by a similar procedure to that described for the preparation of 4-(4-chlorophenyl)propionophenone as Example 19, except that an equivalent amount of isobutyryl chloride was used in place of propionyl chloride. There was thus obtained 4-(4-chlorophenyl)isobutyrophenone, m.p. 76°-77° C. (after recrystallisation from ethanol).

EXAMPLE 11 (All parts by weight)

A mixture of finely powdered 2-{2-[4-(4-chlorophenyl)phenyl]ethoxy}propionic acid (200 parts) was thoroughly mixed with lactose (300 parts) and 9 parts of 10% (weight per volume) aqueous gelatin solution. The mixture was then granulated and the granules mixed with maize starch (100 parts) followed by magnesium stearate (5 parts). The mixture was then compressed into tablets suitable for oral administration for therapeutic purposes.

The aqueous gelatin solution may be replaced if required by a sufficient quantity of 5% (weight per volume) aqueous polyvinylpyrrolidone to effect granulation.

The active ingredient may be replaced by a pharmaceutically acceptable base-addition salt thereof, or by another compound of formula I described in the accompanying Examples, or by a salt thereof.

What is claimed is:

1. A hydroxyalkanoic acid of the formula:

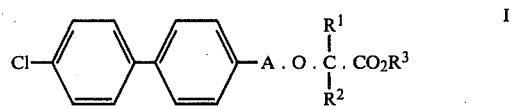

wherein A is an ethylene or trimethylene diradical; $R^1$ is hydrogen, a methyl, ethyl, propyl, isopropyl or butyl radical; and $R^2$ is hydrogen; $R^3$ is hydrogen or a (1–6C)-alkyl radical; or a pharmaceutically acceptable base-addition salt thereof.

2. A compound as claimed in claim 1 wherein $R^3$ is hydrogen or a methyl or ethyl radical.

3. A compound as claimed in claim 1 wherein $R^3$ is hydrogen.

4. 2-{2-[4-(4-Chlorophenyl)phenyl]ethoxy}propionic acid, or a pharmaceutically acceptable base-addition salt thereof.

5. A pharmaceutically acceptable base-addition salt of a compound of formula I as claimed in claim 1 which is an alkali metal or alkaline earth metal salt, an aluminium salt, or a salt of an organic base affording a pharmaceutically acceptable cation.

6. A pharmaceutical composition having anti-arthritic properties which comprises an effective amount of a compound of formula I or a pharmaceutically acceptable base-addition salt thereof, as claimed in claim 1, together with a pharmaceutically acceptable carrier.

7. A method of producing an anti-arthritic effect in a warm-blooded animal requiring such treatment which comprises administering an effective amount of a compound of formula I or a pharmaceutically acceptable base-addition salt thereof, as claimed in claim 1.

* * * * *